US006245317B1

(12) United States Patent
DeGrado et al.

(10) Patent No.: US 6,245,317 B1
(45) Date of Patent: Jun. 12, 2001

(54) F18-LABELED OXA FATTY ACIDS AND METHODS OF MAKING AND USING THE SAME

(75) Inventors: Timothy R. DeGrado; Shuyan Wang, both of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/543,900

(22) Filed: Apr. 6, 2000

Related U.S. Application Data

(60) Provisional application No. 60/129,911, filed on Apr. 19, 1999.

(51) Int. Cl.$^7$ .................................................. A61K 51/00
(52) U.S. Cl. ............................................................ 424/1.89
(58) Field of Search ............................... 424/1.89, 1.85, 424/1.81; 554/226, 228

(56) References Cited

U.S. PATENT DOCUMENTS

| | | | |
|---|---|---|---|
| 4,323,547 | 4/1982 | Knust et al. | 424/1 |
| 4,524,059 | 6/1985 | Elmaleh et al. | 424/1.1 |
| 4,764,358 | 8/1988 | Knapp, Jr. et al. | 424/1.1 |

FOREIGN PATENT DOCUMENTS 3-285689 12/1991 (JP).

OTHER PUBLICATIONS

Scientific Papers, Proceedings of the 44$^{th}$ Annual Meeting, The Journal of Nuclear Medicine, pp. 124–125, Wednesday, Jun. 4, 1997.
Journal of Labelled Compounds and Radiopharmaceuicals, vol. XXIX, No. 9, Synthesis of 14(R,S)–[$^{18}$F] Fluoro–6–Thia–Heptadecamoic Acid (FTHA); Timothy R.. DeGrado, Institut für Chemie 1, Forschungszentrum Jülich, FRG, pp. 989–995, 1991.
8–[$^{18}$F]Fluorooctanoic Acid and its β–Substituted Derivatives as Potential Agents for Cerbral Fatty Acid Studies: Synthesis and Biodistribution, Fumi Nagatsugi, Shigeki Sasaki and Minoru Maeda, Facility of Pharamaeutical Sciences, Xyushu University, Naidashi 3–1–1, Higashi–ku Fukuoka 812, Japan, pp. 809–817, 1994.
14(R,S)–[$^{18}$F]Fluoro–6–Thia–Heptadecanoic Acid (FHTA): Evaluation in Mouse of a New Probe of Myocardial Utilization of Long Chain Fatty Acids, Timothy R. DeGrado, Heinz H. Coenen, and Gerhard Stocklin, Institut fur Chemie 1, Forschungszentrum Julich, Germany, pp. 1888–1896, The Journal of Nuclear Medicine, vol. 32, No. 10, Oct. 1991.

Free Fatty Acid Uptake in the Myocardium and Skeletal Muscle Using Fluorine–18–Fluoro–6–Thia–Heptadecanoic Acid, Maija T. Maki, Merja Haaparanta, Pirjo Nuutila, Vesa Oikonen, Matti Luotolahti, Olli Eskola and Juhani M. Knuuti, Departments of Nuclear Medicine, Medicine and Clinical Physiology, and Radiochemistry Laboratory, University of Turku, Turku, and Turku PET Centre, Turku, Finland, pp. 1320–1327, The Journal of Nuclear Medicine, vol. 39, No. 8, Aug. 1998.
Kinetics of 14(R, S)–Fluorine–18–Fluoro–6–Thia–Heptadecanoic Acid in Normal Human Hearts at Rest, During Exercise and After Dipyridamole Injection, Andreas Ebert, Hans Herzog, Gerhard L. Stocklin, Michael M. Henrich, Timothy R. DeGrado, Heniz H. Coenen and Ludwig E. Feinendegen, Institute fur Medizin und Nuklearchemie, Forschungszentrum Julich, and Nuklennedizinische Klinik der Heinrich–Heine–Universital Dusseldorf, Julich, Germany, pp. 51–56, The Journal of Nuclear Medicine, vol. 35, No. 1, Jan. 1994.
Myocardial Uptake of the Fatty Acid Analog 14–Fluorine–18–Fluoro–6–Thia–Heptadecanoic Acid in Comparison to Beta Oxidation Rates by Tritiated Palmitate, Charles k. Stone, Robert A. Pooley, Timothy R. DeGrado, Britta Renstrom, Robert J. Nickles, Stephen H. Nellis, A. James Liedtke and James E. Holden; Departments of Medicine (Cardiology), Radiology (Nuclear Medicine) and Medical Physics, University of Wisconsin–Madison, Madison, Wisconsin; and Department of Radiology, Duke University, Durham, North Carolina; The Journal of Nuclear Medicine, vol. 39, No. 10, Oct. 1998.
Comparison of Fatty Acid Tracers FTHA and BMIPP During Myocardial Ischemia and Hypoxia, Britta Renstrom, Stephen Rommelfanger, Charles K. Stone, Timothy R. DeGrado, Khristen J. Carlson, Emanual Scarbrough, Robert J. Nickles, A. James Liedtke and James E. Holden; Department of Medicine (Cardiology), Radiology and Medical Physics, University of Wisconsin–Madison, Madison, Wisconsin, and Department of Radiology, Duke University Medical Center, Durham, North Carolina, pp. 1684–1689, The Journal of Nuclear Medicine, vol. 39, No. 10, Oct. 1998.

Primary Examiner—Michael G. Hartley
(74) Attorney, Agent, or Firm—Nixon & Vanderhye P.C.

(57) ABSTRACT

Oxygen substitution at the C3 position of $^{18}$F-labeled fatty acids yields a tracer that is specific to mitochondrial metabolism of fatty acids in liver tissue. Most preferably, the invention is embodied in an [$^{18}$F]fluoro-3-oxa-fatty acid having a chain length of between 8 to 20 carbon atoms. The $^{18}$F-labeled 3-oxa fatty acids of this invention find particular utility the radiolabelling of mammalian liver tissue purposes of positron emission tomography.

8 Claims, No Drawings

F18-LABELED OXA FATTY ACIDS AND METHODS OF MAKING AND USING THE SAME

CROSS-REFERENCE TO RELATED APPLICATION

This application is based on, and claims domestic priority benefits under 35 USC §119(e) from, U.S. Provisional Patent Application Ser. No. 60/129,911 filed on Apr. 19, 1999, the entire content of which is expressly incorporated hereinto by reference.

FIELD OF THE INVENTION

The present invention relates to $^{18}$F-labeled oxa fatty acids, and to methods of making and using the same, in particular, to methods of using such fatty acids as a tracer compound in positron emission tomography (PET).

BACKGROUND OF THE INVENTION

A radioiodinated 4-thia fatty acid analog has been previously reported (Gildehaus et al, J Nucl Med 38:124P, 1997, abstract). $^{18}$F-labeled fatty acids are known generally from U.S. Pat. No. 4,323,547 (incorporated hereinto by reference) as useful in PET studies of myocardial metabolism. More recently, $^{18}$F-labeled 6-thia fatty acid (14F6THA) has been synthesized and evaluated (DeGrado, J Lab Compd Radiopharm 24:989–995, 1991; DeGrado et al, J Nucl Med 32:1888–1896, 1991, each incorporated hereinto fully by reference). 4-thia and 6-thia fatty acid analogs track total beta-oxidation of palmitate in the liver. Beta-oxidation of long-chain fatty acids may occur in either mitochondria or peroxisomes. Investigation in isolated rat livers using specific inhibition of carnitine palmitoyl-transferase has suggested that $^{18}$F-labeled 4-thia fatty acids are trapped in the liver tissue in both organelles. A more specific probe of mitochondrial metabolic function is needed.

SUMMARY OF THE INVENTION

It has been discovered that uptake of $^{18}$F-labeled 3-oxa fatty acids correlate with mitochondrial fatty acid oxidation in the liver. The present invention therefore is embodied in $^{18}$F-labeled fatty acids having oxa-substitution at the C3 position of the chain. Most preferably, the invention is embodied in an [$^{18}$F]fluoro-3-oxa-fatty acids having a chain length of between 8 to 20 carbon atoms.

The $^{18}$F-labeled 3-oxa fatty acids of this invention find particular utility as tracers of hepatic mitochondrial beta-oxidation in mammalian livers with positron emission tomography (PET). In this regard, beta-oxidation of long chain fatty acids is a primary source of ATP for the liver. The total distribution volume of long-chain $^{18}$F-labeled 3-oxa fatty acids correlates with mitochondrial beta-oxidation rate.

A 3-oxa fatty acid analog of this invention may be used alone or in combination with other metabolic or perfusion tracers. For example, PET imaging in the same subject may be accomplished using both a 3-oxa fatty acid and a 4-thia fatty acid analog of the type disclosed more completely in copending U.S. patent application Ser. No. 09/543,899 filed even date herewith in the name of the same inventors as the present application and entitled "F$^{18}$-Labeled Thia Fatty Acids and Methods of Making and Using the Same", the entire content of which is expressly incorporated hereinto by reference. PET imaging using both 3-oxa and a 4-thia fatty acid tracers may provide information on fatty acid oxidation specifically in mitochondria and peroxisomes.

PET measurements of hepatic beta-oxidation rates should provide important information on the metabolic function of the liver in a number of disease states including alcoholic steatohepatitis, non-alcoholic steatohepatitis, obesity and type-2 diabetes. Of particular interest is the possibility that inhibition of fatty acid oxidation is a contributory factor in the accumulation of complex lipids in fatty liver diseases. The specificity of the 3-oxa fatty acid accumulation to hepatic mitochondria may allow differential diagnosis of diseases that affect the mitochondria in liver.

A further understanding of this invention will be obtained from the following non-limiting Examples.

EXAMPLES

Chemicals used in the following Examples were of analytical grade. Dry acetonitrile was obtained commercially (Pierce, Rockford, Ill.). $^1$H-NMR spectra were recorded with a Varian Unity 500 MHz spectrometer using CDCl$_3$ as solvent (Me$_4$Si, 0.00 ppm). R$_f$ values refer to thin layer chromatography (TLC) performed on silica gel with the solvent system noted. Routine column chromatography was performed under normal pressure with silica gel (100–200 mesh) and the solvent system noted.

t-Butyl 15-Hydroxy-3-oxa-pentadecanoate (1)

12-tetrahydropyranyloxy-1-dododecanol was synthesized from 1,12-dodecanediol as previously described (Sonnet, et al, Stereoisomers and analogs of 14-methyl-1-octadecene, sex pheromone of peach leafminer moth, *Lyonetia clerkella*, L. J Chem Ecol 13:547–555, 1987, incorporated hereinto by reference).

This alcohol (5 mmol) was caused to react with t-butyl bromoacetate (20 mmol) and tetrabutylammonium hydrogen sulfate (5 mmol) in 20 ml 50% NaOH and 15 ml CHCl$_2$ at room temperature for 4 hours. The solution was extracted twice with ether, and the organic phase was dried (MgSO$_4$), and evaporated under reduced pressure. The product of this reaction, t-butyl 15-tetrahydropyranyloxy-3-oxa-pentadecanoate, was isolated by liquid chromatography (hexane/ethyl acetate 3:1), R$_f$=0.7. This product was directly reacted in methanol with a catalytic amount of p-toluenesulfonic acid for 2 hours at room temperature. After neutralization of the solution with sodium bicarbonate, the solvent was evaporated. Ether (20 ml) and brine (20 ml) were added, and the organic layer was dried (MgSO$_4$) and evaporated under reduced pressure. The product 1 (3.3 mmol, 66%) was isolated as a colorless oil by liquid chromatography (hexane/ethyl acetate 3:1), R$_f$=0.2. $^1$H-NMR 1.2–1.65 (m, 20H, CH$_2$), 1.48 (s, 9H, (t-butyl) CH$_3$), 3.50 (t, 2H, C(4) H$_2$), 3.64 (t, 2H, C(15)H$_2$), 3.94 (s, 3H, C(2)H$_2$).

t-Butyl 15-Tosyloxy-3-oxa-pentadecanoate (2)

To 3 mmol of product 1 in dichloromethane (10 ml) was added tosyl chloride (5 mmol) and pyridine (5 mmol) and the solution was stirred at room temperature for 20 hours. Ether (20 ml) and dilute HCl was added, and the organic layer washed successively with water and brine, dried (MgSO$_4$), and evaporated under reduced pressure. The product 2 was isolated as an oil in 90% yield by column chromotography (hexane/ethyl acetate 3:1). TLC (hexane/ethyl acetate 2:1) R$_f$=0.5. $^1$H-NMR 1.2–1.65 (m, 20H, CH$_2$), 1.48 (s, 9H, (t-butyl) CH$_3$), 2.45 (s, 3H, (tosyl) CH$_3$), 3.50 (t, 2H, C(4)H$_2$), 3.94 (s, 3H, —COO—CH$_3$), 4.02 (t, 2H, C(15)H$_2$), 7.6 (m, 4H, aryl).

t-Butyl 15-Bromo-3-oxa-pentadecanoate (3)

To 2 mmol of product 2 in acetone was added lithium bromide (7 mmol) and the solution was stirred at room temperature for 4 hours. Ether (20 ml) and dilute HCl was added, and the organic layer washed successively with water and brine, dried (MgSO$_4$), and evaporated under reduced pressure. The product 3 was isolated as an oil in 85% yield by column chromotography (hexane/ethyl acetate 4:1). TLC (hexane/ethyl acetate 3:1) R$_f$=0.8. $^1$H-NMR 1.2–1.65 (m, 20H, CH$_2$), 1.48 (s, 9H, (t-butyl) CH$_3$), 3.41 (t, 2H, C(15) H$_2$), 3.50 (t, 2H, C(4)H$_2$), 3.94 (s, 3H, C(2)H$_2$).

15-Fluoro-3-oxa-pentadecanoic Acid (4, FOP)

To 5 ml of a 1M solution of tetrabutylammonium fluoride in THF was added 1.15 mmol of tosylate 2. The solution was stirred at room temperature for 4 hours. Ether (20 ml) and water (20 ml) were added, and the organic phase was dried (MgSO$_4$) and evaporated under reduced pressure. The resultant fluoro-ester was isolated by column chromatography (hexane/ethyl acetate 3:1). TLC (hexane/ethyl acetate 3:1) R$_f$=0.7. The methyl ester was directly hydrolyzed in 20 ml ethanol/ 0.2 N KOH (1:1) at room temperature overnight. After evaporation of the majority of the ethanol, ether (30 ml) and dilute HCl were added. The organic layer was washed with brine, dried (MgSO$_4$), and evaporated under reduced pressure. The product 4 was crystallized in 60% yield from hexane. Melting point=38° C. $^1$H-NMR 1.2–1.65 (m, 20H, CH$_2$), 3.50 (t, 2H, C(4)H$_2$), 3.94 (s, 3H, C(2)H$_2$), 4.44 (dt, 2H, C(15)H$_2$ J$_{HF}$=47.5 Hz, J$_{HH}$=6.2 Hz).

Methyl 15-Bromo-3-oxa-pentadecanoate (5)

To 1.3 mmol of 3 in methanol (20 ml) was added a catalytic amount of p-toluenesulfonic acid and the solution was stirred under reflux for 5 hr. Ether (20 ml) and water (20 ml) were added, and the organic layer washed successively with water and brine, dried (MgSO$_4$), and evaporated under reduced pressure. The product 5 (1 mmol, 77%) was isolated as an oil by column chromatography (hexane/ethyl acetate 9:1->3:1). TLC (hexane/ethyl acetate 3:1) R$_f$=0.6. $^1$H-NMR 1.2–1.65 (m, 20H, CH$_2$), 3.41 (t, 2H, C(15)H$_2$), 3.50 (t, 2H, C(4)H$_2$), 3.72 (s, 3H, —COO—CH$_3$), 3.94 (s, 3H, C(2)H$_2$).

$^{18}$F-labeling Procedure

The precursor for F-18 labeled FTP and FOP is the compound of products 5. To a 2 ml glass vial was added kryptofix 2.2.2 (10 mg), acetonitrile (0.5 ml) and 20 ml of a 9% K$_2$CO$_3$ solution in water. [$^{18}$F]Fluoride, produced via proton bombardment of H$_2$$^{18}$O (>95 atom %), was then added, the vessel placed in an aluminum heating block at 85 EC, and the solvent evaporated under a stream of helium or nitrogen. The residue was further dried by azeotropic distillation with acetonitrile (2×0.3 ml). A solution of the precursor (~2 mg) in acetonitrile (0.5 ml) was added, the vial was sealed and returned to the heating block. Reaction time was 15 min. The vial was briefly cooled by placing in ice-water. The incorporation of [$^{18}$F]fluoride was monitored by radio-TLC (hexane/ethyl acetate 3:1). R$_f$ values were 0.0 and 0.7 for [$^{18}$F]fluoride and [$^{18}$F]fluoro-ester, respectively.

Subsequent hydrolysis of the resulting [$^{18}$F]fluoro-ester was performed in the same vessel by the addition of 0.2 ml 0.2N KOH and continued heating at 90° C. for 4 min. The mixture was cooled, acidified with concentrated acetic acid (25 ml), filtered, and applied to the preparative HPLC column (Table 1). An in-line UV-detector (210 nm) was used to monitor the elution of unlabeled materials. The [$^{18}$F] fluoro-fatty acid fraction was collected, evaporated to dryness, formulated in isotonic NaCl solution (for long-chain fatty acid analogs, 1–2% albumin was present), and filtered through a 0.22 mm filter (Millex-GS).

TABLE 1

Semi-preparative reverse phase HPLC capacity factors (k =) of fatty acid analogs (Nucleosil, C-18 (10 m), 250 × 10 mm, flow = 4.3 ml/min, mobile phase is MeOH/H$_2$O/AcOH X:Y:0.5, X + Y = 99.5)

| Compound | Mobile Phase (% MeOH) | k' |
|---|---|---|
| 15-Bromo-3-oxa-pentadecanoic acid | 85 | 4.2 |
| 15-Fluoro-3-oxa-pentadecanoic acid (FOP) | 85 | 3.1 |

Biological Studies

Experiments were performed in live rats (biodistributions) and isolated rat livers with a model long chain 3-oxa analog (15-[$^{18}$F]fluoro-3-oxa-pentadecanoic acid=FOP). The perfusate was Krebs-Hensleit buffer with 1% albumin, 0.15 mM palmitate, and 5 mM glucose. Sprague Dawley rats (200–225 g) were fasted overnight. The portal vein was cannulated and perfused at 8 ml/min. The livers were then dissected free from the carcass of the animal and placed between two NaI(Tl) scintillation probes. The perfusate was gassed with either 95% oxygen (normoxic) or 35% oxygen (hypoxic) gas mixture. The gases comprising the remaining fraction were nitrogen and carbon dioxide (5% for both). The tracer was administered as a bolus or as a pulse infusion for 20 minutes. Pulse infusion allowed absolute quantification of $^{18}$F uptake rates by the liver. Uptake and clearance rates are measured by fitting of the hepatic time-activity curves to a two-compartment model. Distribution volumes of the two compartments are estimated from the fitted rate constants. Beta-oxidation rates of 9,10 [$^3$H]palmitate were measured by collection of venous effluent samples and separation of titrated water. Results showed good correlation of beta-oxidation rates with distribution volumes of compartment 2 (V2) (r=0.95) and total distribution volume of FOP in liver (V_total=V1+V2) (r=0.96). The linear fit of the plot of V_total (ml/g liver) versus palmitate oxidation (ml/min/g dry) gives the equation y=−2.35+13.7x. The intercept is not statistically significant from zero (p=0.09). Biodistribution of FOP in rats measured at 15 and 30 minutes after injection showed high uptake by liver tissue, and relatively low levels of radioactivity in blood, heart, kidney and other tissues. Thus, the uptake of FOP appeared to be specific to mitochondrial metabolism of fatty acids in liver.

PET imaging studies were performed in healthy male and female subjects and in patients with non-alcoholic steatohepatitis (NASH). The NASH patients showed decreased uptake of FOP consistent with dysfunction of mitochondrial metabolism.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An $^{18}$F-labeled 3-oxa substituted fatty acid tracer of chain length between 8 to 20 carbon atoms that exhibits uptake specific to mitochondrial metabolism of fatty acids in liver tissue.

2. The $^{18}$F-labeled 3-oxa substituted fatty acid tracer of claim 1, which is saturated.

3. The $^{18}$F-labeled 3-oxa substituted fatty acid tracer of claim 1, which is at least partially unsaturated.

4. The $^{18}$F-labeled 3-oxa substituted fatty acid tracer of claim 1, which includes a fatty acid moiety which is pentadecanoic acid.

5. The $^{18}$F-labeled 3-oxa substituted fatty acid tracer of claim 1, wherein the [$^{18}$F]fluorine atom is substituted at the terminal carbon.

6. 15-[$^{18}$F]fluoro-3-oxa-pentadecanoic acid which exhibits uptake specific to mitochondrial metabolism of fatty acids in liver tissue.

7. A method of radiolabeling mammalian liver tissue which comprises administering to a mammal a radiolabeling effective amount of the $^{18}$F-labeled oxa fatty acid substituted tracer according to any one of claims 1 and 2–6.

8. A positron emission tomography technique which comprises radiolabeling mammalian liver tissue according to claim 7, and thereafter subjecting the radiolabeled liver tissue to positron emission tomography, and generating an image therefrom.

* * * * *

UNITED STATES PATENT AND TRADEMARK OFFICE
CERTIFICATE OF CORRECTION

PATENT NO. : 6,245,317 B1
DATED : June 12, 2001
INVENTOR(S) : Timothy R. DeGrado et al.

It is certified that error appears in the above-identified patent and that said Letters Patent is hereby corrected as shown below:

Column 3,
Line 10, change "tosylate 2" to -- bromide 5 --;
Line 67, change "mm" to -- $\mu$m --;

Column 4,
Line 3, change "(k =)" to -- ($k^1$ =) --;

Signed and Sealed this

Twenty-fourth Day of December, 2002

JAMES E. ROGAN
*Director of the United States Patent and Trademark Office*